United States Patent
Muppaneni et al.

(10) Patent No.: US 11,840,610 B2
(45) Date of Patent: *Dec. 12, 2023

(54) COMPOSITIONS AND METHODS FOR THE DEGRADATION OF WASTE POLYPROPYLENE

(71) Applicant: Novoloop, Inc., Menlo Park, CA (US)

(72) Inventors: Tapaswy Muppaneni, Newark, CA (US); Russell Pratt, San Mateo, CA (US); Jennifer Le Roy, Mountain View, CA (US)

(73) Assignee: Novoloop, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/839,078

(22) Filed: Jun. 13, 2022

(65) Prior Publication Data

US 2022/0306829 A1 Sep. 29, 2022

Related U.S. Application Data

(63) Continuation of application No. PCT/US2020/064439, filed on Dec. 11, 2020.

(60) Provisional application No. 62/946,837, filed on Dec. 11, 2019.

(51) Int. Cl.
*C08J 11/26* (2006.01)

(52) U.S. Cl.
CPC ............ *C08J 11/26* (2013.01); *C08J 2323/12* (2013.01)

(58) Field of Classification Search
USPC ......................................................... 521/47
See application file for complete search history.

(56) References Cited

U.S. PATENT DOCUMENTS

| | | |
|---|---|---|
| 2,824,122 A | 2/1958 | Kuceski |
| 2,824,123 A | 2/1958 | Kuceski et al. |
| 2,824,134 A | 2/1958 | Hill et al. |
| 3,810,937 A | 5/1974 | Kuceski |
| 4,251,500 A | 2/1981 | Morita et al. |
| 4,515,659 A | 5/1985 | Wingfield et al. |
| 5,414,169 A | 5/1995 | Takahashi et al. |
| 5,811,606 A | 9/1998 | Yang |
| 5,821,396 A | 10/1998 | Bouziane |
| 7,626,061 B2 | 12/2009 | Datsevich et al. |
| 7,758,729 B1 | 7/2010 | Dewhitt et al. |
| 7,959,890 B2 | 6/2011 | MacIntosh et al. |
| 8,344,195 B2 | 1/2013 | Srinakruang |
| 8,425,731 B2 | 4/2013 | Ali et al. |
| 8,927,797 B2 | 1/2015 | Sarker et al. |
| 10,519,292 B2 | 12/2019 | Yao et al. |
| 10,557,011 B2 * | 2/2020 | Yao ..................... C07C 69/42 |
| 11,028,217 B1 | 6/2021 | Knauer et al. |
| 11,111,334 B1 | 9/2021 | Higginson et al. |
| 11,192,999 B2 | 12/2021 | Yao et al. |
| 11,220,586 B2 | 1/2022 | Yao et al. |
| 2002/0103301 A1 | 8/2002 | Yoshida et al. |
| 2003/0195374 A1 | 10/2003 | Herwig et al. |
| 2012/0261247 A1 | 10/2012 | McNamara et al. |
| 2014/0371385 A1 | 12/2014 | Verberne et al. |
| 2015/0001061 A1 | 1/2015 | Bordynuik |
| 2017/0137365 A1 | 5/2017 | Wampler et al. |
| 2019/0322834 A1 * | 10/2019 | Yao ..................... C07C 69/48 |
| 2022/0119616 A1 | 4/2022 | Yao et al. |

FOREIGN PATENT DOCUMENTS

| | | | |
|---|---|---|---|
| CN | 101279906 A | 10/2008 | |
| CN | 108473390 A | 8/2018 | |
| EP | 1201728 A2 | 5/2002 | |
| FR | 2972346 A1 * | 9/2012 | ............... A61K 8/37 |
| JP | S50117714 A | 9/1975 | |
| JP | S54119401 A | 9/1979 | |
| JP | 2002212334 A | 7/2002 | |
| JP | 2003306465 A | 10/2003 | |
| JP | 2015533932 A | 11/2015 | |
| WO | WO-2007101929 A1 * | 9/2007 | ............ C07C 67/22 |
| WO | WO-2008058303 A1 | 5/2008 | |
| WO | WO-2012117250 A1 | 9/2012 | |
| WO | WO-2012119861 A2 * | 9/2012 | ............... A61K 8/37 |
| WO | WO-2014031305 A1 | 2/2014 | |
| WO | WO-2014040634 A1 | 3/2014 | |
| WO | WO-2016209193 A1 | 12/2016 | |
| WO | WO-2017003802 A1 | 1/2017 | |
| WO | WO-2019204687 A1 | 10/2019 | |
| WO | WO-2021076845 A1 | 4/2021 | |
| WO | WO-2021119389 A1 | 6/2021 | |
| WO | WO-2021183883 A1 | 9/2021 | |
| WO | WO-2021183891 A1 | 9/2021 | |

OTHER PUBLICATIONS

WO-2007101929-A1 machine translation (Year: 2007).*
FR-2972346-A1 machine translation (Year: 2012).*
Drain, K.F., et al., "A solvent technique for the recycling of polypropylene—degradation on recycling," Conservation & Recycling 6(3): 123-137, Elsevier, Netherlands (Feb. 1983).
International Search Report and Written Opinion for International Application No. PCT/US2020/064439, European Patent Office, Netherlands, dated Apr. 14, 2021, 15 pages.
M.D Salvador, et al. "Evaluation of chemical degradation of commercial polypropylene" Journal of Materials Processing Technology, vols. 143-144, Dec. 20, 2003, pp. 693-697.

* cited by examiner

*Primary Examiner* — Terressa Boykin
(74) *Attorney, Agent, or Firm* — Helene Laville; HEFIP, LLC

(57) ABSTRACT

Disclosed are methods for polypropylene decomposition. Also disclosed are products obtained from the decomposition polypropylene including carboxylic acids, dicarboxylic acids, nitro-substituted carboxylic acids and dicarboxylic acids; as well as the salts, esters, and anhydrides thereof.

30 Claims, No Drawings

COMPOSITIONS AND METHODS FOR THE DEGRADATION OF WASTE POLYPROPYLENE

CROSS-REFERENCE TO RELATED PATENT APPLICATIONS

This application is a continuation of International Application No. PCT/US2020/064439, filed Dec. 11, 2020, which claims the benefit of U.S. Provisional Application No. 62/946,837, filed Dec. 11, 2019, both of which are incorporated herein by reference in their entirety.

FIELD OF THE INVENTION

This invention relates to the field of plastic waste decomposition and recycling. More specifically, the invention comprises methods for the decomposition of polypropylene (PP) and the products obtained by decomposition of PP, including carboxylic acids, dicarboxylic acids, carboxylic acids substituted by a nitro group, dicarboxylic acids substituted by a nitro group; and the salts, esters and anhydrides thereof.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Plastic pollution is a global environmental crisis for many reasons. Plastics are made to be durable rather than degradable. The ones that are biodegradable demonstrate shortcomings such as high production costs and functionality problems, which result in their challenges to be produced or used on a large scale. Furthermore, the existence of a large variety of plastic polymer types has led to an increase in public confusion on the subject of what is recyclable. Plastic consumerism is inevitable and continues to grow. Not only is existing plastic pollution prevalent and ubiquitous, but new plastic waste is generated at an alarming rate. This global excess of plastic waste harms the environment and pollutes the food chain.

A common component of the municipal waste stream and marine debris is contaminated plastics or contaminated plastic waste. Current methods that exist for the treatment of contaminated plastics or contaminated plastic waste include pyrolysis, incineration, landfill disposal, and mechanical recycling after thorough cleaning. Plastic pyrolysis is energy intensive and produces low-grade fuels that require expensive refinery steps to be useful chemicals. This cannot be economically accomplished. Plastic incineration requires massive amounts of upfront capital to establish, needs substantial power and maintenance, and also results in adverse environmental consequences, as does the disposal of plastics in landfills. These expensive methods pollute the environment and do not utilize the contaminated plastic waste materials that could be used as a raw feedstock for new products. Almost all post-consumer and post-industrial contaminated plastic waste are centralized to material recovery facilities, where they can become further contaminated. Mechanical recycling for many plastics is not economically viable because recycled plastic resins often have compromised quality and cannot compete with cheap virgin plastics.

Less than 10% of global plastics produced is recycled because the process is not economical. As much as 50% of recycling bin content in the United States is considered contamination and is normally discarded by the traditional recycling process. Even though plastics are the most abundant materials in the waste recovery stream, they are the least preferred material for recycling because most plastics, with the exception of water bottles, have few or no viable downstream markets.

Although much research has been done on the bioremediation of plastic pollution, biological methods alone are expensive, inefficient, and difficult to scale. Such techniques, including those involving ex vivo cellular degradation or insect larval digestion, also have not coupled plastic waste treatment with the production of value-added economical products.

Polypropylene (PP) is one of the most common packaging materials used in the United States thanks to its melting point and high strength. In 2017 approximately 8% of PP plastic generated in the United States was recycled. There are several reasons for the low recycling rate of PP which includes the high cost of recycling, the comparatively low cost of virgin PP and the reduced quality of recycled PP compared to virgin.

There are two main categories of recycling technologies that are currently used to recycle PP. Mechanical recycling technologies clean the polymers and create new PP feedstock that can be used to manufacture new products. The basic mechanical recycling process comprises of several steps which can include collection, sorting, cleaning, melting processing and formation of new material. In some instances, solvent-based separation procedures are implemented to remove impurities from post-use plastics. See WO2012/117250A1, WO2017/003802A1, and WO2008/058303A1. In many instances, the harsh conditions PP is subjected to during mechanical recycling results in downgraded PP compared to virgin PP.

Chemical recycling technologies are also currently in use to convert post-use PP into fuel or energy. See, WO2014/040634A1 and WO2016/091993A1. Such technologies are typically high energy and they result in low carbon efficiency.

Thus, there is a need in the art for methods and systems that provide for the decomposition of PP waste that overcome the limitations of known methods.

SUMMARY OF THE INVENTION

The following embodiments and aspects thereof are described and illustrated in conjunction with compositions and methods which are meant to be exemplary and illustrative, not limiting in scope.

Provided is a method for decomposing polypropylene (PP) waste, comprising:
 a. adding PP waste to a reaction vessel;
 b. adding at least one oxidizing agent to the reaction vessel to give a mixture; and
 c. subjecting the mixture obtained in b. to conditions effective to decompose the PP waste to produce decomposition products, wherein the decomposition products comprise at least one dicarboxylic acid optionally substituted by a nitro group; or the salts or esters or anhydrides thereof.

In one embodiment, the decomposition products further comprise at least one carboxylic acid, optionally substituted by a nitro group.

In one embodiment, the PP waste further comprises at least one plastic material; and at least one non-plastic material. In another embodiment, wherein the plastic material comprises at least one selected from the group consisting of plastic film, plastic foam, plastic packaging, plastic bags, plastic wrap, and combinations thereof. In another embodiment, the non-plastic material comprises at least one selected from the group consisting of non-plastic organic material, inorganic material, fluid, and combinations thereof.

In some embodiments, the at least one oxidizing agent is oxygen ($O_2$), nitric oxide (NO), nitrous oxide ($N_2O$), nitrogen dioxide ($NO_2$), nitric acid ($HNO_3$), aqueous nitric acid ($HNO_3$), or combinations thereof. In one embodiment, the at least one oxidizing agent is aqueous nitric acid ($HNO_3$). In another embodiment, the nitric acid has a concentration of 10-100 wt %. In one embodiment, the nitric acid has a concentration of about 67 to about 70 wt %.

In some embodiments, the weight ratio of nitric acid to PP is at least 3:1. In one embodiment, the weight ratio of nitric acid to PP is at least 10:1. In another embodiment, the weight ratio of nitric acid to PP is 10-100:1.

In one embodiment, the conditions comprise a temperature range from 60° C. to 200° C. In another embodiment, the conditions comprise an initial pressure range of 0 psi to 1000 psi. In another embodiment, the conditions comprise the presence of a gas that is at least one selected comprising air, nitrogen ($N_2$), oxygen ($O_2$), or combinations thereof. In another embodiment, the conditions comprise a residence time in the reaction vessel of 30 minutes to 30 hours.

In one embodiment, the dicarboyxlic acid or dicarboxylic acid substituted with at least one nitro group is substituted with one or more methyl groups.

In one embodiment, the decomposition products comprise at least one $C_4$-$C_{15}$ dicarboxylic acid. In another embodiment, the decomposition products comprise at least one $C_4$-$C_9$ dicarboxylic acid. In another embodiment, wherein when the dicarboxylic acid comprises a carbon chain of an even number n between the two carboxy groups, it is substituted by (n/2)-1 methyl groups. In another embodiment, wherein when the dicarboxylic acid comprises a carbon chain of an odd number n between the two carboxy groups, it is substituted by (n/2)-1 or (n/2)-2 methyl groups.

In one embodiment, the decomposition products obtained from the method comprise at least one of 2-methylsuccinic acid, 3-methylglutaric acid, 2,4-dimethylglutaric acid, 2,4-dimethyladipic acid, 3,5-dimethylpimelic acid, 2,4,6-trimethylpimelic acid, 2,4,6-trimethylsebacic acid, and 2,4,6,8-tetramethyl-azelaic acid. In another embodiment, the decomposition products further comprise at least one of Butanedioic acid, methyl-, dimethyl ester; Butanedioic acid, methyl-, dimethyl ester; Butanedioic acid, methyl-, dimethyl ester; Pentanedioic acid, 2,4-dimethyl-, dimethyl ester; 1,4-Benzenedicarbonitrile, 2-formyl-1H-; Pentanedioic acid, 2,4-dimethyl-, dimethyl ester; 5-Acetoxy-3-methylhexanoic acid, methyl ester; 9-Decenoic acid, 2,4-dimethyl-, methyl ester, (R,R)-(−)-; Heptanedioic acid, 2-methyl-, dimethyl ester;

Heptanedioic acid, 3,5-dimethyl-, dimethyl ester; Quinoline, 2-butyl; Cyclohexanecarboxylic acid, ethyl ester; 3-Cyclobut-1-enyl-hydroxy-2-methyl-propionic acid, methyl ester; Adipic acid, methyl propyl ester; Methyl 2-methyl-3-cyclopropylpropanoate; 2-Propanone, 1-cyclopentyl-3-ethoxy-; Cyclohexane, 1,2-diethyl-, cis-; Cyclohexane, 1,2-diethyl-3-methyl-; Octanedioic acid, 2,2,7,7-tetramethyl-; 9-Decenoic acid, 2,4-dimethyl-, methyl ester, (2S, 4R)-(+)-; O-Fluoroacetophenone oxime; Dibenzo[b,f]oxepin-3-ylamine; Carbamic acid, (4-ethoxyphenyl)-, ethyl ester; Quinoline, 2-(1-methyl-1H-imidazol-4-yl); 2,8-Bis(1,5,5-trimethylpyrrolidin-2,4-dion-3-ylidene)-3,7-diazanonan; 2-Amino-3,5,7,8-tetrahydro-4,6-pteridinedione; or 1,2-Dimethoxy-4-(1,2-dimethoxyethyl)benzene.

In one embodiment, the carboxylic acid or dicarboxylic acid obtained from the method is substituted with at least one nitro group. In another embodiment, the carboxylic acid or dicarboxylic acid is substituted in the 2-position with the nitro group. In another embodiment, the carboxylic acid or dicarboxylic acid is substituted in the 3-position with the nitro group. In another embodiment, the carboxylic acid or dicarboxylic acid is substituted at an internal position with the nitro group.

In one embodiment, the method further comprises adding at least one solid state catalyst to the reaction vessel. In another embodiment, the at least one solid state catalyst is selected from the group consisting of zeolite, alumina, silico-alumino-phosphate, sulfated zirconia, zinc oxide, titanium oxide, zirconium oxide, niobium oxide, iron carbonate, calcium carbide, and combinations thereof.

In one embodiment, the method further comprises separating the decomposition products into a solid phase and a liquid phase. In another embodiment, the solid phase comprises at least one selected from the group consisting of oligomer, polymer, and combinations thereof. In another embodiment, the solid phase further comprises at least one solid state catalyst.

In one embodiment, the liquid phase comprises a carboxylic acid, dicarboxylic acid, carboxylic acid substituted with a nitro group, or dicarboxylic acid substituted with a nitro group, or the salt, or ester or anhydride thereof.

In one embodiment, the method further comprises converting the carboxylic acid optionally substituted with a nitro group and/or the dicarboxylic acid optionally substituted with a nitro group into an ester.

In one embodiment, the method further comprises separating the carboxylic acid optionally substituted with a nitro group and/or the dicarboxylic acid optionally substituted with a nitro group, or the salts, or esters or anhydrides thereof. In another embodiment, the method further comprises separating the at least one corresponding ester. In one embodiment, the ester is at least one of 2-methylsuccinic acid, dimethyl ester; 3-methylglutaric acid, dimethyl ester; 2,4-dimethylglutaric acid, dimethyl ester; 2,4-dimethyladipic acid, dimethyl ester; 3,5-diethylpimelic acid, dimethyl ester; 2,4,6-trimethylpimelic acid, dimethyl ester; 4,6-trimethylsebacic acid, dimethyl ester; 2,4,6,8-tetramethyl-azelaic acid; or a combination thereof.

In one embodiment, the method further comprises feeding the oligomer, the polymer, and combinations thereof back into the reaction vessel.

In one embodiment, the liquid phase further comprises the at least one oxidizing agent. In another embodiment, method further comprises collecting and regenerating the at least one oxidizing agent.

Also provided is a composition, comprising 2-methylsuccinic acid, 3-methylglutaric acid, 2,4-dimethylglutaric acid, 2,4-dimethyladipic acid, 3,5-dimethylpimelic acid, 2,4,6-trimethylpimelic acid, 2,4,6-trimethylsebacic acid, and 2,4,6,8-tetramethyl-azelaic acid, or the salts, or esters or anhydrides thereof. In one embodiment, the composition further comprises at least one of Butanedioic acid, methyl-dimethyl ester; Butanedioic acid, methyl-, dimethyl ester; Butanedioic acid, methyl-, dimethyl ester; Pentanedioic acid, 2,4-dimethyl-, dimethyl ester; 1,4-Benzenedicarbonitrile, 2-formyl-1H-; Pentanedioic acid, 2,4-dimethyl-, dimethyl ester; 5-Acetoxy-3-methyl-hexanoic acid, methyl ester; 9-Decenoic acid, 2,4-dimethyl-, methyl ester, (R,R)-(−)-; Heptanedioic acid, 2-methyl-, dimethyl ester; Heptanedioic acid, 3,5-dimethyl-, dimethyl ester; Quinoline, 2-butyl; Cyclohexanecarboxylic acid, ethyl ester; 3-Cyclobut-1-enyl-hydroxy-2-methyl-propionic acid, methyl ester; Adipic acid, methyl propyl ester; Methyl 2-methyl-3-cyclopropyl-propanoate; 2-Propanone, 1-cyclopentyl-3-ethoxy-; Cyclohexane, 1,2-diethyl-, cis-; Cyclohexane, 1,2-diethyl-3-methyl-; Octanedioic acid, 2,2,7,7-tetramethyl-; 9-Decenoic acid, 2,4-dimethyl-, methyl ester, (2S, 4R)-(+)-; O-Fluoroacetophenone oxime; Cyclohexanone, 2-(1-mercapto-1-methylethyl)-5-methyl-, trans-; Dibenzo[b,f]oxepin-3-ylamine; Carbamic acid, (4-ethoxyphenyl)-, ethyl ester; Quinoline, 2-(1-methyl-1H-imidazol-4-yl)-; 2,8-Bis(1,5,5-trimethylpyrrolidin-2,4-dion- 3 -ylidene)-3,7-diazanonan; 2-Amino-3,5,7,8-tetrahydro-4,6-pteridinedione; or 1,2-Dimethoxy-4-(1,2-dimethoxyethyl)benzene, or the salts or the esters or the anhydrides thereof.

DETAILED DESCRIPTION OF THE INVENTION

All references cited herein are incorporated by reference in their entirety as though fully set forth. Unless otherwise defined, all technical and scientific terms used herein have the same meaning as commonly understood by one of ordinary skill in the art to which this invention belongs.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

As used herein the term "comprising" or "comprises" is used in reference to compositions, methods, systems, articles of manufacture, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). As used herein, the term "comprising" or "comprises" means that other elements can also be present in addition to the defined elements presented. The use of "comprising" indicates inclusion rather than limitation. Although the open-ended term "comprising" as a synonym of terms such as including, containing, or having, is used herein to describe and claim the invention, the present invention, or embodiments thereof, may alternatively be described using alternative terms such as "consisting of" or "consisting essentially of".

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

Groupings of alternative elements or embodiments of the present invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

"Optional" or "optionally" means that the subsequently described circumstance may or may not occur, so that the description includes instances where the circumstance occurs and instances where it does not.

As used herein, the term "substituted" refers to independent replacement of one or more (typically 1, 2, 3, 4, or 5) of the hydrogen atoms on the substituted moiety with substituents independently selected from the group of substituents listed below in the definition for "substituents" or otherwise specified. In general, a non-hydrogen substituent can be any substituent that can be bound to an atom of the given moiety that is specified to be substituted. Examples of substituents include, but are not limited to, acyl, acylamino, acyloxy, aldehyde, alicyclic, aliphatic, alkanesulfonamido, alkanesulfonyl, alkaryl, alkenyl, alkoxy, alkoxycarbonyl, alkyl, alkylamino, alkylcarbanoyl, alkylene, alkylidene, alkylthios, alkynyl, amide, amido, amino, amidine, aminoalkyl, aralkyl, aralkylsulfonamido, arenesulfonamido, arenesulfonyl, aromatic, aryl, arylamino, arylcarbanoyl, aryloxy, azido, carbamoyl, carbonyl, carbonyls including ketones, carboxy, carboxylates, $CF_3$, cyano (CN), cycloalkyl, cycloalkylene, ester, ether, haloalkyl, halogen, halogen, heteroaryl, heterocyclyl, hydroxy, hydroxyalkyl, imino, iminoketone, ketone, mercapto, nitro, oxaalkyl, oxo, oxoalkyl, phosphoryl (including phosphonate and phosphinate), silyl groups, sulfonamido, sulfonyl (including sulfate, sulfamoyl and sulfonate), thiols, and ureido moieties, each of which may optionally also be substituted or unsubstituted. In some cases, two substituents, together with the carbon(s) to which they are attached to, can form a ring. In some cases, two or more substituents, together with the carbon(s) to which they are attached to, can form one or more rings.

Substituents may be protected as necessary and any of the protecting groups commonly used in the art may be employed. Non-limiting examples of protecting groups may be found, for example, in Greene and Wuts, Protective Groups in Organic Synthesis, 44th. Ed., Wiley & Sons, 2006.

The term "carboxy" means the radical —C(O)O—. It is noted that compounds described herein containing carboxy moiety can include protected derivatives thereof, i.e., where the oxygen is substituted with a protecting group. Suitable protecting groups for carboxy moieties include benzyl, tent-butyl, methyl, ethyl, and the like. The term "carboxyl" means —COOH.

The term "polymer" means a substance, chemical compound or mixture of compounds, that has a molecular structure consisting chiefly or entirely of a large number of similar units (e.g., monomer units) bonded together. Of which, linear polymer is also called straight-chain because it consists of a long string of carbon-carbon bonds; branching polymer has branches at irregular intervals along the polymer chain; cross linking polymer contains branches that connect polymer chains, via covalent, ionic, or H-bonding; optionally substituted polymer is a polymer that contains functionality at random points along the hydrocarbon chain backbone where one or more of the hydrogen atoms linked to the chain backbone may be, but are not required to be substituted with a substituent independently selected from the group of substituents provided herein in the definition for "substituents" or otherwise specified. Such polymers are said to be optionally substituted because they generally do not exhibit a regular substitution pattern along the chain backbone; addition polymer is formed by adding monomers to a growing polymer chain; condensation polymer is formed when a small molecule condenses out during the polymerization reaction; homopolymer is formed by polymerizing a single monomer; copolymer is formed by polymerizing more than one monomer; synthetic polymer is synthesized through chemical reactions; natural polymer is originated in nature and can be extracted; biopolymer is produced by living organisms, modified or natural; organic polymers are polymers that contain carbon atoms in the backbone of the polymer chain.

The term "oligomer" means a substance, chemical compound or mixture of compounds that has a molecular structure consisting chiefly or entirely of a few number of similar units (e.g., monomer units) bonded together.

The term "plastic" means a synthetic material comprising a wide range of organic polymers such as polyolefins, polyesters, polyamides, etc., that can be molded into shape while soft and then set into a rigid, semi-elastic, or elastic form. One example of a plastic is polypropylene (PP).

The term "about" means the recited number ±10%. For example, "about 100" means 90-110, inclusive.

Various Non-Limiting Embodiments of the Invention

It is an object of the present invention to provide methods and systems that provide for the decomposition of PP waste that overcome the limitations of known methods and systems.

The present invention provides methods for the degradation of PP that provide low molecular weight oxidized monomers. These monomers can be used to synthesize higher value materials. Such monomers include short-chain dicarboxylic acids that are building blocks for materials including, but not limited to, polyamides and polyurethanes. In addition, the low molecular weight carboxylic acids and mixtures of acids may be transformed by bacterial into new products such as lipids, oils, pigments and proteins.

In various embodiments, the present invention provides a method for decomposing PP waste, comprising: adding PP waste to a first reaction vessel; adding at least one oxidizing agent to the first reaction vessel; subjecting the PP waste to conditions effective to decompose the PP waste to produce a decomposition mixture in the first reaction vessel. In some embodiments, the method further comprises producing at least one first off-gas. In some embodiments, the method further comprises collecting and regenerating the oxidizing agent. In some embodiments, the method further comprises transferring the decomposition mixture to a first distillation unit. In some embodiments, the method further comprises removing at least a portion of the oxidizing agent from the decomposition mixture to form a decomposition slurry. In some embodiments, the decomposition slurry comprises at least one compound containing at least one carboxyl group; and at least one residual oxidizing agent. In some embodiments, the at least one compound containing at least one carboxyl group is at least one organic acid. In some embodiments, the method further comprises transferring the decomposition slurry to a second reaction vessel. In some embodiments, the method further comprises adding at least one alcohol to the second reaction vessel to form an esterification reaction mixture; and subjecting the esterification reaction mixture to conditions effective to form an esterification product mixture. In some embodiments, the esterification product mixture comprises at least one residual oxidizing agent, at least one alcohol, and at least one ester. In some embodiments, the method further comprises transferring the esterification product mixture to a second distillation unit. In some embodiments, the method further comprises separating the esterification product mixture in the second distillation unit into a residual oxidizing agent waste stream, an ester stream, and an alcohol stream. In some embodiments, the ester stream comprises at least one organic acid in at least one ester form. In some embodiments, the method further comprises adding at least one solid state catalyst to the first reaction vessel. In some embodiments, the method comprises optionally adding at least one solid state catalyst to the first reaction vessel. In some embodiments, the method may include adding at least one solid state catalyst to the first reaction vessel.

In various embodiments, the present invention provides a method for decomposing PP waste, comprising: adding PP waste to a reaction vessel; adding at least one oxidizing agent to the reaction vessel; and subjecting the PP waste to conditions effective to decompose the PP waste to produce a decomposition mixture. In some embodiments, the method further comprises adding at least one solid state catalyst to the reaction vessel. In some embodiments, the method comprises optionally adding at least one solid state catalyst to the reaction vessel. In some embodiments, the method may include adding at least one solid state catalyst to the reaction vessel. In some embodiments, the conditions comprise a temperature range; an initial pressure range of a gas; and a residence time in the reaction vessel.

In various embodiments, the present invention provides a method for decomposing PP waste, comprising: adding PP waste to a reaction vessel; adding at least one oxidizing agent to the reaction vessel; optionally adding at least one solid state catalyst to the reaction vessel; and subjecting the PP waste to conditions effective to decompose the PP waste to produce a decomposition mixture. In some embodiments, the conditions comprise a temperature range; an initial pressure range of a gas; and a residence time in the reaction vessel.

In various embodiments, the present invention provides a method for decomposing PP waste, comprising: adding PP waste to a reaction vessel; adding at least one oxidizing agent to the reaction vessel; optionally adding at least one solid state catalyst to the reaction vessel; and subjecting the PP waste to conditions effective to decompose the PP waste to produce a decomposition mixture, wherein the conditions comprise: a temperature range; an initial pressure range of a gas; and a residence time in the reaction vessel.

In some embodiments, the method is selected from the group consisting of a batch process, continuous process, substantially continuous process, and semi-continuous process.

In some embodiments, the present invention provides a system for decomposing PP waste, comprising: a first reaction vessel; a condenser; an abatement unit; an enricher unit; a first distillation unit; a second reaction vessel; and a second distillation unit; wherein the first reaction vessel is connected to the condenser and to the first distillation unit; the condenser is connected to the abatement unit and to the first reaction vessel; the abatement unit is connected to the enricher unit; the enricher unit is connected to the abatement unit; the first distillation unit is connected to the enricher unit and to the second reaction vessel; the second reaction vessel is connected to the second distillation unit; and the second distillation unit is connected to the second reaction vessel.

Reaction Vessel

Non-limiting examples of a reaction vessel (e.g., reactors, glass lined reactors, glass flasks, containers and the like in which the methods and/or processes of the present invention are performed) suitable for use in a processes and/or methods of the invention are generally closed (not open to the surrounding atmosphere) and, optionally, pressurizable reactors; non-limiting types of closed, pressurizable reactors suitable for, in particular, batch processes, continuous processes, substantially continuous processes, or semi-continuous processes according to the invention include reactors and autoclaves from Parr Instrument Company, Amar Equipments, Buchiglas, and Berghof. In some embodiments, the reaction vessel is pressurized. In some embodiments, the reaction vessel is not pressurized.

In some embodiments, the reaction vessel is at least one selected from the group consisting of reactor, glass flask, glass lined reactor, and combinations thereof.

In some embodiments relevant types of reaction vessels for performing batch processes or continuous processes, substantially continuous processes, or semi-continuous processes include substantially vertically disposed reaction vessels in which the PP waste and any additional reagents/materials (e.g. gases, liquids, solids) in question may be contained and into which gases may be introduced-continuously or at intervals-under pressure or at ambient pressure via one or more inlets, ports, valves or the like situated at or near the bottom of, and/or at other locations along the length of, the reaction vessel; such reaction vessels, which may suitably, but optionally, have an upper headspace or free volume, may be essentially cylindrical, tubular or of any other appropriate form. In some embodiments, reaction vessels for performing batch processes or continuous processes, substantially continuous processes, or semi-continuous processes include substantially horizontally disposed reactors.

In batch processes, continuous processes, substantially continuous processes, or semi-continuous processes it is generally desirable, where possible, to cause mixing of the PP waste and any additional reagents/materials (e.g. gases, liquids, solids) and any solid phase and any liquid phase and any gas phase which may be present in the reaction vessel. In some embodiments, the PP is added in the form of solid, melted, or shredded PP. In some embodiments mixing may suitably be achieved by mechanical stirring, although agitation of the reaction vessel as a whole or other means of causing mixing may be applicable. In some embodiments, mixing may be suitably achieved by recirculation by means of a pump, impeller wheel, rotating scraper, or the like.

Heat may be supplied to the reaction mixture and/or reaction system (e.g., the PP waste and any additional reagents/materials (e.g. gases, liquids, solids) and any solid phase and any liquid phase and any gas phase which may be present in the reactor) by any suitable method. Non-limiting examples include immersing the reaction vessel in an appropriate heating bath (comprising, e, g., an oil, a molten salt or molten salt mixture, superheated steam, etc.); by means of thermally conductive (typically metal) tubing which is wound around the outside of the reaction vessel, and/or is immersed in the reaction medium itself, and through which suitably hot oil, superheated steam or the like is passed; or-similarly-by means of one or more electrical resistance heating elements wound around the outside of the reaction vessel and/or immersed in the reaction medium; by a heating mantle; or by means of a jacketed reactor as known in the art. Other applicable methods of heating include induction heating (e. g. of a metal reactor casing) and microwave heating.

In some embodiments, the reaction is carried out in a batch process. In other embodiments, the reaction is carried out in a continuous process.

In a batch process, in some embodiments, oxidizing agent (e.g., nitric acid) is added to the reactor before heating and stirring begins. As the reactor reaches the desired temperature, the PP is added and the reaction is allowed to proceed with stirring for the desired time. In some embodiments, the PP is added in the form of solid, melted, or shredded PP. In some embodiments, the oxidizing agent (e.g., nitric acid) is refluxed in the reaction vessel using a condenser during the process. After the reaction is complete, the reactor is left to cool and the reaction mixture (comprising liquid and solid streams), are filtered, e.g., through filter paper, a sieve, Buchner funnel or the like. The solid stream comprises unreacted or incompletely reacted PP. The liquid stream comprises dilute nitric acid, dissolved dicarboxylic acids and other compounds such as nitro-substituted dicarboxylic acids. In some embodiments, the liquid stream is then heated and the oxidizing agent (e.g., nitric acid) and water are separated from the dicarboxylic acids by distillation.

In a continuous process, in some embodiments, the initial desired amount of oxidizing agent (e.g., nitric acid) is added to the reactor before heating a stirring begins. As the reactor reaches the desired temperature, the PP is added. In some embodiments, the PP is added in the form of solid, melted, or shredded PP. The reaction vessel exit valve is then opened and adjusted so that the amount of product exiting the reaction vessel is at a constant flow rate that is about the same as the amounts of PP and oxidizing agent being added to the reaction vessel, thus maintaining about a constant amount of reactants and products in the reaction vessel during the process. In some embodiments, the oxidizing agent (e.g., nitric acid) is refluxed in the reaction vessel using a condenser during the process. In some embodiments, samples are taking at time intervals, cooled, and filtered, e.g., through filter paper, with a sieve, Buchner funnel or the like. The liquid stream comprises dilute nitric acid, dissolved dicarboxylic acids and other compounds such as nitro-substituted dicarboxylic acids. In some embodiments, the liquid stream is then heated and the oxidizing agent (e.g., nitric acid) and water are separated from the dicarboxylic acids by distillation.

Temperature Range

In some embodiments, the temperature range is from 60° C. to 225° C. In some embodiments, the temperature range in the reaction vessel is from 60° C. to 200° C. In some embodiments, the reaction vessel is the first reaction vessel.

In some embodiments, the temperature range is from 60° C. to 200° C., 60° C. to 175° C., 60° C. to 150° C., 60° C. to 125° C., 60° C. to 100° C., 60° C. to 90° C., 60° C. to 80° C., or 60° C. to 70° C.

In some embodiments, the temperature range is from 60° C. to 200° C., 70° C. to 200° C., 80° C. to 200° C., 90° C. to 200° C., 100° C. to 200° C., 100° C. to 200° C., 120° C. to 200° C., 130° C. to 200° C., 140° C. to 200° C., 150° C. to 200° C., 160° C. to 200° C., 170° C. to 200° C., 180° C. to 200° C., or 190° C. to 200° C.

Initial Pressure Range of a Gas

In some embodiments, the initial pressure of the gas is 0 psi to 1000 psi. In some embodiments, the initial pressure of the gas in the reaction vessel is 0 psi to 1000 psi. In some embodiments, the reaction vessel is the first reaction vessel.

In some embodiments, the initial pressure of the gas is 0 psi to 900 psi, 0 psi to 800 psi, 0 psi to 700 psi, 0 psi to 600 psi, 0 psi to 500 psi, 0 psi to 400 psi, 0 psi to 300 psi, 0 psi to 200 psi, or 0 psi to 100 psi.

Residence Time in the Reaction Vessel

In some embodiments, the residence time in the reaction vessel is one selected from the group consisting of 30 minutes to 30 hours, less than 30 minutes, and more than 30 hours. In some embodiments, the reaction vessel is the first reaction vessel.

In some embodiments the residence time in the reaction vessel is 30 minutes to 30 hours, 30 minutes to 29 hours, 30 minutes to 28 hours, 30 minutes to 27 hours, 30 minutes to 26 hours, 30 minutes to 25 hours, 30 minutes to 24 hours, 30 minutes to 23 hours, 30 minutes to 22 hours, 30 minutes to 21 hours, 30 minutes to 20 hours, 30 minutes to 19 hours, 30 minutes to 18 hours, 30 minutes to 17 hours, 30 minutes to 16 hours, 30 minutes to 15 hours, 30 minutes to 14 hours, 30 minutes to 13 hours, 30 minutes to 12 hours, 30 minutes to 11 hours, 30 minutes to 10 hours, 30 minutes to 9 hours, 30 minutes to 8 hours, 30 minutes to 7 hours, 30 minutes to 6 hours, 30 minutes to 5 hours, 30 minutes to 4 hours, 30 minutes to 3 hours, 30 minutes to 2 hours, or 30 minutes to 1 hour.

In some embodiments, the residence time in the reaction vessel is 30 minutes, 25 minutes, 20 minutes, 15 minutes, 10 minutes, or 5 minutes.

In some embodiments, the residence time in the reaction vessel is 30 hours, 35 hours, 40 hours, 45 hours, 50 hours, 55 hours, 60 hours, 65 hours, 70 hours, or 75 hours. In some embodiments, the residence time in the reaction vessel is about 1 hour to about 10 hours. In some embodiments, the residence time in the reaction vessel is about 3 hours to about 6 hours.

Effects of Time, Temperature, Pressure and Concentration

Different products and amounts of products are obtained depending on the time, temperature and pressure of the reaction.

Oxidizing Agent

In some embodiments, the at least one oxidizing agent is selected from the group consisting of oxygen ($O_2$), nitric oxide (NO), nitrous oxide ($N_2O$), nitrogen dioxide ($NO_2$), nitric acid ($HNO_3$), aqueous nitric acid ($HNO_3$), and combinations thereof.

In some embodiments, the aqueous nitric acid has a concentration of 10%-100% by weight, 10%-90% by weight, 10%-80% by weight, 10%-70% by weight, 10%-60% by weight, 10%-50% by weight, 10%-40% by weight, 10%-30% by weight, or 10%-20% by weight.

In some embodiments, the aqueous nitric acid has a concentration of 10%-100% by weight, 20%-100% by weight, 30%-100% by weight, 40%-100% by weight, 50%-100% by weight, 60%-100% by weight, 70%-100% by weight, 80%-100% by weight, or 90%-100% by weight. In some embodiments, the aqueous nitric acid has a concentration of about 67 to about 70% by weight.

Solid State Catalyst

In some embodiments, the at least one solid state catalyst is selected from the group consisting of zeolite, alumina, silico-alumino-phosphate, sulfated zirconia, zinc oxide, titanium oxide, zirconium oxide, niobium oxide, iron carbonate, calcium carbide, and combinations thereof.

Contaminated PP Waste

In various embodiments, without limitation the PP waste may be contaminated by other plastics and/or non-plastic waste and may be obtained from at least one of the following sources: municipal waste or marine debris.

The term "municipal waste," commonly known as trash, garbage, refuse, or rubbish, refers to a waste type consisting of various items that are discarded by the public. The composition of municipal solid waste can comprise various waste types and can vary from municipality to municipality and can also change over time. In some embodiments municipal solid waste can further comprise at least one other waste type such as biodegradable waste, recyclable materials, inert waste, electrical and electronic waste, composite wastes, contaminated plastic waste, and combinations thereof.

The term "marine debris" refers to human created waste type that has deliberately or accidentally been released in a lake, river, sea, ocean, canal, or waterway. In some instances, marine debris may be mixed with naturally occurring materials (e.g., driftwood, kelp, microorganisms, etc.). In some embodiments, marine debris comprises at least one contaminated plastic waste.

The term "contaminated PP waste" means any PP and/or PP material that is used and/or produced and subsequently discarded, wherein the PP and/or PP material is mixed or contaminated with at least one plastic and/or non-plastic material. In various embodiments, contaminated PP waste comprises at least one PP material; and at least one non-plastic material. In various embodiments, contaminated PP waste consists of at least one PP material; and at least one non-plastic material. In various embodiments, contaminated PP waste consists essentially of at least one PP material; and at least one non-plastic material.

Non-limiting examples of biodegradable waste include food and kitchen waste, green waste, paper, etc. Non-limiting examples of recyclable materials include paper, cardboard, glass, bottles, jars, tin cans, aluminum cans, aluminum foil, metals, certain plastics, fabrics, clothes, tires, batteries, etc. Non-limiting examples of inert waste include construction and demolition waste, dirt, rocks, debris, sand, concrete. Non-limiting examples of electrical and electronic waste include electrical appliances, light bulbs, washing machines, TVs, computers, screens, mobile phones, alarm clocks, watches, etc. Non-limiting examples of composite wastes include waste clothing, toys, etc.

Plastic Material

In various embodiments, the PP material comprises at least one selected from the group consisting of PP film, PP foam, PP packaging, PP bags, PP wrap, and combinations thereof. In some embodiments, the PP material is at least one selected from the group consisting of PP film, PP foam, PP packaging, PP bags, PP wrap, and combinations thereof.

Non-Plastic Material

In the broadest sense, the non-plastic material is any material that is not plastic or a plastic material. Non-limiting examples of non-plastic materials include non-plastic organic materials, inorganic materials, fluids (non-plastic fluids), etc. In various embodiments, the non-plastic material comprises at least one selected from the group consisting of non-plastic organic material, inorganic material, fluid, and combinations thereof.

Non-Plastic Organic Material

In some embodiments, the non-plastic organic material is at least one selected from the group consisting of plant material, animal material, algae material, bacteria material, fungus material, virus material, biological material, cellulose material, cellulose based material, cellulose containing material, and combinations thereof.

As used herein, the term "biological material" denotes a material originating, taken, isolated, derived, and/or obtained from a biological organism.

In some embodiments, the non-plastic organic material is at least one selected from the group consisting of plant derived material, animal derived material, algae derived material, bacteria derived material, fungus derived material, virus based material, biological derived material, and combinations thereof.

In some embodiments, the non-plastic organic material is at least one cellulose based material. In some embodiments, the at least one cellulose based material is at least one selected from the group consisting of paper-based materials, paper, paperboard, wood, engineered wood, plant fibers, textile, fabric, and combinations thereof.

Inorganic Material

In the broadest sense, the term "inorganic material" generally means materials that are not organic compounds or organic materials. Non-limiting examples of inorganic materials include rocks, minerals, glass, ceramics, metals, etc.

Fluid

Non-limiting examples of fluids include water, hydrocarbons, synthetic fluids, naturally derived fluids, acids, bases, or biological fluids, or any mixtures or combinations thereof.

In some embodiments, the fluid is at least one selected from the group consisting of water, hydrocarbons, synthetic fluids, naturally derived fluids, acids, bases, biological fluids, and combinations thereof.

Non-limiting examples of water include salt water, sea water, fresh water, reclaimed water, recycled water, or waste water, or any mixtures or combinations thereof.

In some embodiments, the water is at least one selected from the group consisting of salt water, sea water, fresh water, reclaimed water, recycled water, waste water, and combinations thereof.

Decomposition Mixture

In various embodiments, the decomposition mixture comprises a solid phase and a liquid phase.

In various embodiments, the solid phase comprises at least one selected from the group consisting of oligomer, polymer, and combinations thereof.

In various embodiments, the solid phase further comprises at least one solid state catalyst. In some embodiments, the solid phase optionally comprises at least one solid state catalyst. In some embodiments, the solid phase may include at least one solid state catalyst.

In various embodiments, the liquid phase comprises at least one compound comprising at least one carboxyl group. In various embodiments, the liquid phase comprises at least one compound containing at least one carboxyl group and, optionally, at least one nitro group.

In various embodiments, the at least one compound comprising at least one carboxyl group is at least one organic acid. In various embodiments, the at least one compound containing at least one carboxyl group is at least one organic acid.

In some embodiments, the at least one organic acid is at least one selected from the group consisting of optionally substituted organic acid, substituted organic acid, and unsubstituted organic acid.

In some embodiments, the at least one organic acid is at least one selected from the group consisting of monocarboxylic acid, dicarboxylic acid, polycarboxylic acid, and combinations thereof.

In some embodiments, the at least one monocarboxylic acid is at least one selected from the group consisting of optionally substituted monocarboxylic acid, substituted monocarboxylic acid, unsubstituted monocarboxylic acid, and combinations thereof.

In some embodiments, the at least one dicarboxylic acid is at least one selected from the group consisting of optionally substituted dicarboxylic acid, substituted dicarboxylic acid, unsubstituted dicarboxylic acid, and combinations thereof.

In some embodiments, the at least one polycarboxylic acid is at least one selected from the group consisting of optionally substituted polycarboxylic acid, substituted polycarboxylic acid, unsubstituted polycarboxylic acid, and combinations thereof.

In some embodiments, the at least one organic acid is at least one $\alpha,\omega$-dicarboxylic acid.

In some embodiments, the at least one $\alpha,\omega$-dicarboxylic acid is at least one selected from the group consisting of optionally substituted $\alpha,\omega$-dicarboxylic acid, substituted $\alpha,\omega$-dicarboxylic acid, unsubstituted $\alpha,\omega$-dicarboxylic acid, and combinations thereof. Optionally, the at least one $\alpha,\omega$-dicarboxylic acid is substituted by at least one nitro group. The nitro group may be substituted at the 2-, 3-, or an internal position of the carboxylic acid chain. In addition, the at least one $\alpha,\omega$-dicarboxylic acid may be in the form of an anhydride.

In some embodiments, the $\alpha,\omega$-dicarboxylic acid is a $C_4$-$C_{15}$ dicarboxylic acid. In other embodiments, the $\alpha,\omega$-dicarboxylic acid is a $C_4$-$C_9$ dicarboxylic acid. In other embodiments, when the dicarboxylic acid comprises a carbon chain of an even number n between the two carboxy groups, it is substituted by (n/2)-1 methyl groups. In other embodiments, when the dicarboxylic acid comprises a carbon chain of an odd number n between the two carboxy groups, it is substituted by (n/2)-1 or (n/2)-2 methyl groups. All stereoisomers are possible. In other embodiments, the $\alpha,\omega$-dicarboxylic acid substituted with methyl groups is substituted by one or more nitro groups. In some embodiments, the $\alpha,\omega$-dicarboxylic acid substituted with methyl groups is substituted by one or more nitro groups at the 2-, 3, 4, or other internal position of the α,ω-dicarboxylic acid.

In some embodiments, the at least one organic acid is at least one selected from succinic acid, glutaric acid, adipic acid, pimelic acid, suberic acid, azelaic acid, sebacic acid, undecanedioic acid, dodecanedioic acid, and combinations thereof. The at least one organic acid is optionally substituted by one or more methyl groups.

In some embodiments, the decomposition mixture comprises a composition comprising at least one of succinic acid, glutaric acid, adipic acid, pimelic acid, suberic acid, azelaic acid, sebacic acid, undecanedioic acid, dodecanedioic acid, and combinations thereof. The succinic acid, glutaric acid, adipic acid, pimelic acid, suberic acid, azelaic acid, sebacic acid, undecanedioic acid, and dodecanedioic acid are optionally substituted by one ore more methyl groups.

In some embodiments, the liquid phase comprises a composition comprising at least one of succinic acid, glutaric acid, adipic acid, pimelic acid, suberic acid, azelaic acid, sebacic acid, undecanedioic acid, dodecanedioic acid, and combinations thereof. The succinic acid, glutaric acid, adipic acid, pimelic acid, suberic acid, azelaic acid, sebacic acid, undecanedioic acid, and dodecanedioic acid are optionally substituted by one or more methyl groups.

In some embodiments, the liquid phase comprises a composition comprising at least one of 2-methyl succinic acid, 3-methylglutaric acid, 2,4-dimethylglutaric acid, 2,4-dimethyladipic acid, 3,5-dimethylpimelic acid, 2,4,6-trimethylpimelic acid, 2,4,6-trimethyl sebacic acid, 2,4,6,8-tetramethyl-azelaic acid.

In some embodiments, the liquid phase comprises a composition comprising at least one of Butanedioic acid, methyl-, dimethyl ester; Butanedioic acid, methyl-, dimethyl ester; Butanedioic acid, methyl-, dimethyl ester; Pentanedioic acid, 2,4-dimethyl-, dimethyl ester; 1,4-Benzenedicarbonitrile, 2-formyl-1H-Cyclopenta[c]thiophene, hexahydro-, cis-; Pentanedioic acid, 2,4-dimethyl-, dimethyl ester; 1H-Cyclopenta[c]thiophene, hexahydro-, cis-; Furan, 2-methyl-5-(methylthio)-; 5-Acetoxy-3-methyl-hexanoic acid, methyl ester; 9-Decenoic acid, 2,4-dimethyl-, methyl ester, (R,R)-(−)-; Heptanedioic acid, 2-methyl-, dimethyl ester; Heptanedioic acid, 3,5-dimethyl-, dimethyl ester; Quinoline, 2-butyl; Cyclohexanecarboxylic acid, ethyl ester; 3-Cyclobut-1-enyl-hydroxy-2-methyl-propionic acid, methyl ester; Adipic acid, methyl propyl ester; Methyl 2-methyl-3-cyclopropylpropanoate; 2-Propanone, 1-cyclopentyl-3-ethoxy-; Cyclohexane, 1,2-diethyl-, cis-; Cyclohexane, 1,2-diethyl-3-methyl-; Octanedioic acid, 2,2,7,7-tetramethyl-; 9-Decenoic acid, 2,4-dimethyl-, methyl ester, (2S,4R)-(+)-; O-Fluoroacetophenone oxime; meta-Methoxybenzenethiol; Cyclohexanone, 2-(1-mercapto-l-methylethyl)-5-methyl-, trans-; Benzenethiol, 4-methoxy-; Dibenzo[b,f]oxepin-3-ylamine; Carbamic acid, (4-ethoxyphenyl)-, ethyl ester; Quinoline, 2-(1-methyl-1H-imidazol-4-yl)-; 2,8-Bis(1,5,5-trimethylpyrrolidin-2,4-dion-3-ylidene)-3,7-diazanonan; 2-Amino-3,5,7,8-tetrahydro-4,6-pteridinedione; and 1,2-Dimethoxy-4-(1,2-dimethoxyethyl) benzene.

In some embodiments, the method further comprises separating the at least one organic acid.

Non-limiting examples of separation techniques include simple distillation, fractional distillation, azeotropic distillation, co-distillation, fractional crystallization, standard crystallization, lyophilization, supercritical fluid extraction, solvent extraction, precipitation, and combinations thereof. In some embodiments, the separating is carried out by at least one selected from the group consisting of simple distillation, fractional distillation, azeotropic distillation, co-distillation, fractional crystallization, standard crystallization, lyophilization, supercritical fluid extraction, solvent extraction, precipitation, and combinations thereof.

Esterification

The conversion of at least one compound containing at least one carboxyl group (e.g., an organic acid) from an acid form to an ester occurs by a process commonly known in the art as esterification. In some embodiments, the conversion of the at least one compound containing at least one carboxyl group from an acid form to an ester form is performed under esterification conditions. In some embodiments, the dicarboxylic acids are at least partially in the form of esters.

In some embodiments, the method further comprises converting the at least one organic acid into at least one corresponding ester. In some embodiments, the at least one corresponding ester is at least one selected from the group consisting of methyl ester, ethyl ester, propyl ester, isopropyl ester, butyl ester, isobutyl ester, sec-butyl ester, tert-butyl ester, pentyl ester, and hexyl ester, and combinations thereof. In some embodiments, the at least one corresponding ester is a methyl ester. In some embodiments, the converting is carried out by esterification or esterifying.

In some embodiments, the method further comprises combining the at least one organic acid with at least one alcohol to form an esterification mixture; and subjecting the esterification mixture to conditions effective to form at least one ester. Any suitable esterification conditions known in the art may be used to form the at least one ester. For example, the at least one organic acid can be admixed with at least one alcohol and the admixture heated to cause esterification. A mineral acid may be added as a catalyst.

In some embodiments, the at least one alcohol is at least one selected from a group consisting of linear alcohol, branched alcohol, cyclic alcohol, and combinations thereof. In some embodiments, the at least one alcohol is at least one selected from the group consisting of methanol, ethanol, propanol, isopropanol, butanol, isobutanol, sec-butanol, tent-butanol, pentanol, hexanol, and combinations thereof. In some embodiments, the at least one alcohol is a $C_1$-$C_{10}$ alcohol. In some embodiments, the at least one alcohol is a $C_1$-$C_4$ alcohol. In some embodiments, the at least one alcohol is methanol.

In some embodiments, the at least one organic acid is independently in at least one ester form. In some embodiments, the at least one ester or ester form is at least one selected from the group consisting of methyl ester, ethyl ester, propyl ester, isopropyl ester, butyl ester, isobutyl ester, sec-butyl ester, tent-butyl ester, pentyl ester, and hexyl ester, and combinations thereof. In some embodiments, the at least one ester form or ester is a methyl ester.

In some embodiments, the at least one organic acid is in an ester form. In some embodiments, the α,ω-dicarboxylic acids are in an ester form. In some embodiments the succinic acid is in an ester form. In some embodiments, the glutaric acid is in an ester form. In some embodiments, the adipic acid is in an ester form. In some embodiments, the pimelic acid is in an ester form. In some embodiments the suberic acid is in an ester form. In some embodiments, the azelaic acid is in an ester form. In some embodiments, the sebacic acid is in an ester form. In some embodiments, the undecanedioic acid is in an ester form. In some embodiments, the dodecanedioic acid is in an ester form.

In some embodiments, the succinic acid, glutaric acid, adipic acid, pimelic acid, suberic acid, and azelaic acid are each independently in an ester form.

In some embodiments, the oxalic acid, suberic acid, sebacic acid, undecanedioic acid, dodecanedioic acid, tridecanedioic acid, tetradecanedioic acid, pentadecanedioic acid, 2-octenedioic acid, 2-nonenedioic acid, 2-decenedioic acid, and 2-undecenedioic acid are independently in an ester form.

In some embodiments, the nitro-suberic acid, nitro-azelaic acid, nitro-sebacic acid, nitro-undecanedioic acid, nitro-dodecanedioic acid, nitro-brassylic acid, nitro-tetradecanedioic acid, nitro-pentadecanedioic acid, nitro-hexadecanedioic acid, nitro-heptadecanedioic acid, nitro-octadecanedioic acid, nitro-nonadecanedioic acid, and nitro-icosanedioic acid are independently in an ester form.

In some embodiments, the $C_8$-$C_{20}$ dicarboxylic acid substituted with a single nitro group is in an ester form. In some embodiments, the $C_8$-$C_{20}$ dicarboxylic acid substituted with a single nitro group in the form of an ester is nitro-suberic acid, nitro-azelaic acid, nitro-sebacic acid, nitro-undecanedioic acid, nitro-dodecanedioic acid, nitro-brassylic acid, nitro-tetradecanedioic acid, nitro-pentadecanedioic acid, nitro-hexadecanedioic acid, nitro-heptadecanedioic acid, nitro-octadecanedioic acid, nitro-nonadecanedioic acid, or nitro-icosanedioic acid. In some embodiments, the $C_8$-$C_{20}$ dicarboxylic acid is substituted in the 2-, 3-, or other internal position. In some embodiments, the $C_8$-$C_{20}$ dicarboxylic acid is 2-nitro-suberic acid, 2-nitro-azelaic acid, 2-nitro-sebacic acid, 2-nitro-undecanedioic acid, 2-nitro-dodecanedioic acid, 2-nitro-brassylic acid, 2-nitro-tetradecanedioic acid, 2-nitro-pentadecanedioic acid, 2-nitro-hexadecanedioic acid, 2-nitro-heptadecanedioic acid, 2-nitro-octadecanedioic acid, 2-nitro-nonadecanedioic acid, or 2-nitro-icosanedioic acid, or the salts or esters thereof. In some embodiments, the $C_8$-$C_{20}$ dicarboxylic acid is 3-nitro-suberic acid, 3-nitro-azelaic acid, 3-nitro-sebacic acid, 3-nitro-undecanedioic acid, 3-nitro-dodecanedioic acid, 3-nitro-brassylic acid, 3- nitro-tetradecanedioic acid, 3-nitro-pentadecanedioic acid, 3-nitro-hexadecanedioic acid, 3-nitro-heptadecanedioic acid, 3-nitro-octadecanedioic acid, 3-nitro-nonadecanedioic acid, or 3-nitro-icosanedioic acid, or the salts or esters thereof. In some embodiments, the ester form is selected from the group consisting of monoester, diester, multiester, mixed diester, mixed multiester, and combinations thereof.

The term "multiester" as used herein means an ester formed by converting more than one carboxyl group from an acid form to an ester form under esterification conditions.

In some embodiments, the ester form comprises a α,ω-diester, optionally substituted α,ω-dicarboxylic acid, or substituted α,ω-dicarboxylic acid, unsubstituted α,ω-dicarboxylic acid, and combinations thereof.

In some embodiments, the at least one ester comprises dimethyl succinate, dimethyl glutarate, dimethyl adipate, dimethyl pimelate, dimethyl suberate, dimethyl azelate, dimethyl sebacate, dimethyl undecanedioate, dimethyl dodecanedioate, dimethyl oxalate, dimethyl tridecanedioate, dimethyl tetradecanedioate, dimethyl pentadecanedioate, dimethyl 2-octendioate, dimethyl 2-nonendioate, 2-dimethyl 2-decendioate, dimethyl 2-undecendioate, dimethyl 2-nitro-suberate, dimethyl 2-nitro-azelate, dimethyl 2-nitro-sebacate, dimethyl 2-nitro-undecanedioate, dimethyl 2-nitro-dodecanedioate, dimethyl 2-nitro-brassylate, dimethyl 2-nitro-heptadecanedioate, dimethyl 2-nitro-octadecanedioate, dimethyl 2-nitro-tetradecanedioate, dimethyl 2-nitro-pentadecanedioate, dimethyl 2-nitro-hexadecanedioate, 2-nitro-heptadecanedioate, dimethyl 2-nitro-suberate, dimethyl 2-nitro-sebacate, dimethyl 2-nitro-undecanedioate, dimethyl 2-nitro-dodecanedioate, dimethyl 2-nitro-tetradecanedioate, and dimethyl 2-nitro-pentadecanedioate, dimethyl 3-octendioate, dimethyl 3-nonendioate, 2-dimethyl 3-decendioate, dimethyl 3-undecendioate, dimethyl 3-nitro-suberate, dimethyl 3-nitro-azelate, dimethyl 3-nitro-sebacate, dimethyl 3-nitro-undecanedioate, dimethyl 3-nitro-dodecanedioate, dimethyl 3-nitro-brassylate, dimethyl 3-nitro-heptadecanedioate, dimethyl 3-nitro-octadecanedioate, dimethyl 3-nitro-tetradecanedioate, dimethyl 3-nitro-pentadecanedioate, dimethyl 3-nitro-hexadecanedioate, 3-nitro-heptadecanedioate, dimethyl 3-nitro-suberate, dimethyl 3-nitro-sebacate, dimethyl 3-nitro-undecanedioate, dimethyl 3-nitro-dodecanedioate, dimethyl 3-nitro-tetradecanedioate, and dimethyl 3-nitro-pentadecanedioate, and combinations thereof.

In some embodiments, the at least one corresponding ester comprises dimethyl succinate, dimethyl glutarate, dimethyl adipate, dimethyl pimelate, dimethyl suberate, dimethyl azelate, dimethyl sebacate, dimethyl undecanedioate, dimethyl dodecanedioate, and combinations thereof.

In some embodiments, the esterification mixture comprises a composition comprising at least one of dimethyl succinate, dimethyl glutarate, dimethyl adipate, dimethyl pimelate, dimethyl suberate, dimethyl azelate, dimethyl sebacate, dimethyl undecanedioate, dimethyl dodecanedioate, and combinations thereof.

In some embodiments, the at least one corresponding ester comprises 2-methylsuccinic acid, dimethyl ester; 3-methylglutaric acid, dimethyl ester; 2,4-dimethylglutaric acid, dimethyl ester; 2,4-dimethyladipic acid, dimethyl ester; 3,5-diethylpimelic acid, dimethyl ester; 2,4,6-trimethylpimelic acid, dimethyl ester; 4,6-trimethyl sebacic acid, dimethyl ester; 2,4,6,8-tetramethyl-azelaic acid; or a combination thereof.

In some embodiments, the esterification mixture comprises a composition comprising at least one of 2-methylsuccinic acid, dimethyl ester; 3-methylglutaric acid, dimethyl ester; 2,4-dimethylglutaric acid, dimethyl ester; 2,4-dimethyladipic acid, dimethyl ester; 3,5-diethylpimelic acid, dimethyl ester; 2,4,6-trimethylpimelic acid, dimethyl ester; 4,6-trimethylsebacic acid, dimethyl ester; 2,4,6,8-tetramethyl-azelaic acid; or a combination thereof.

In some embodiments, the method further comprises separating the at least one corresponding ester. In some embodiments, the separating is carried out by distillation. In some embodiments, the separating of the at least one corresponding ester is carried out by distillation. In some embodiments, the distillation is at least one selected from the group consisting of simple distillation, fractional distillation, vacuum distillation, azeotropic distillation, co-distillation, and combinations thereof.

In some embodiments, the method further comprises converting the at least one compound containing at least one carboxyl group from the ester form to an acid form (e.g., converting the ester form back to the acid form). In some embodiments, the converting of the ester form to the acid form is performed under ester hydrolysis conditions.

Salts

In some embodiments, the methods further comprise converting the at least one dicarboxylic acid into at least one corresponding salt. In some embodiments, the at least one corresponding salt is prepared by reacting with a base to form the ion salt of the at least one dicarboxylic acid. Bases include, but are not limited to, alkali metal salts, alkaline earth metal salts and other metal ions. Exemplary ions include aluminum, calcium, lithium, magnesium, potassium, sodium and zinc in their usual valences. Organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine.

In some embodiments, the dicarboxylic acids are converted into alkaline metal salts. In some embodiments, the dicarboxylic acids are at least partially in the form of an alkaline metal salt. The alkaline metal salts can be made by reacting the dicarboxylic acids with an alkaline metal hydroxide. Exemplary alkaline metal hydroxides include sodium hydroxide, potassium hydroxide and lithium hydroxide. Exemplary alkaline metal salts of the dicarboxylic acids include the sodium, potassium and lithium salts.

In some embodiments, the oxalic acid, suberic acid, sebacic acid, undecanedioic acid, dodecanedioic acid, tridecanedioic acid, tetradecanedioic acid, pentadecanedioic acid, 2-octenedioic acid, 2-nonenedioic acid, 2-decenedioic acid, and 2-undecenedioic acid are independently in the form of an alkaline metal salt.

In some embodiments, the 2-methylsuccinic acid, 3-methylglutaric acid, 2,4-dimethylglutaric acid, 2,4-dimethyladipic acid, 3,5-dimethylpimelic acid, 2,4,6-trimethylpimelic acid, 2,4,6-trimethylsebacic acid, 2,4,6,8-tetramethyl-azelaic acid are in the form of an alkaline metal salt.

In some embodiments, the 2-nitro-suberic acid, 2-nitro-azelaic acid, 2-nitro-sebacic acid, 2-nitro-undecanedioic acid, 2-nitro-dodecanedioic acid, 2-nitro-brassylic acid, 2-nitro-tetradecanedioic acid, 2-nitro-pentadecanedioic acid, 2-nitro-hexadecanedioic acid 2-nitro-heptadecanedioic acid, 2-nitro-octadecanedioic acid, 2-nitro-nonadecanedioic acid, and 2-nitro-icosanedioic acid are in the form of an alkaline metal salt. In some embodiments, the 3-nitro-suberic acid, 3-nitro-azelaic acid, 3-nitro-sebacic acid, 3-nitro-undecanedioic acid, 3-nitro-dodecanedioic acid, 3-nitro-brassylic acid, 3-nitro-tetradecanedioic acid, 3-nitro-pentadecanedioic acid, 3-nitro-hexadecanedioic acid, 3-nitro-heptadecanedioic acid, 3-nitro-octadecanedioic acid, 3-nitro-nonadecanedioic acid, and 3-nitro-icosanedioic acid are in the form of an alkaline metal salt.

In some embodiments, the $C_8$-$C_{20}$ dicarboxylic acid substituted with a single nitro group is in the form of an alkaline metal salt. In some embodiments, the $C_8$-$C_{20}$ dicarboxylic acid substituted with a single nitro group is nitro-suberic acid, nitro-azelaic acid, nitro-sebacic acid, nitro-undecanedioic acid, nitro-dodecanedioic acid, nitro-brassylic acid, nitro-tetradecanedioic acid, nitro-pentadecanedioic acid, nitro-hexadecanedioic acid, nitro-heptadecanedioic acid, nitro-octadecanedioic acid, nitro-nonadecanedioic acid, and nitro-icosanedioic acid in the form of an alkaline metal salt. In some embodiments, the $C_8$-$C_{20}$ dicarboxylic acid is 2-nitro-suberic acid, 2-nitro-azelaic acid, 2-nitro-sebacic acid, 2-nitro-undecanedioic acid, 2-nitro-dodecanedioic acid, 2-nitro-brassylic acid, 2-nitro-tetradecanedioic acid, 2-nitro-pentadecanedioic acid, 2-nitro-hexadecanedioic acid, 2-nitro-heptadecanedioic acid, 2-nitro-octadecanedioic acid, 2-nitro-nonadecanedioic acid, or 2-nitro-icosanedioic acid, 3-nitro-suberic acid, 3-nitro-azelaic acid, 3-nitro-sebacic acid, 3-nitro-undecanedioic acid, 3-nitro-dodecanedioic acid, 3-nitro-brassylic acid, 3-nitro-tetradecanedioic acid, 3-nitro-pentadecanedioic acid, 3-nitro-hexadecanedioic acid, 3-nitro-heptadecanedioic acid, 3-nitro-octadecanedioic acid, 3-nitro-nonadecanedioic acid, or 3-nitro-icosanedioic acid, or the salts or esters thereof.

Some embodiments of the present invention can be defined as any of the following numbered paragraphs:

1. A method for decomposing PP waste, comprising: adding PP waste to a reaction vessel; adding at least one oxidizing agent to the reaction vessel; and subjecting the PP waste to conditions effective to decompose the PP waste to produce a decomposition mixture.

2. The method of paragraph 1, further comprising adding at least one solid state catalyst to the reaction vessel.

3. The method of paragraph 1, wherein the conditions comprise a temperature range; an initial pressure range of a gas; and a residence time in the reaction vessel.

4. The method of paragraph 1, wherein the PP waste comprises at least one plastic material; and at least one non-plastic material.

5. The method of paragraph 4, wherein the plastic material comprises at least one selected from the group consisting of plastic film, plastic foam, plastic packaging, plastic bags, plastic wrap, and combinations thereof.

6. The method of paragraph 4, wherein the non-plastic material comprises at least one selected from the group consisting of non-plastic organic material, inorganic material, fluid, and combinations thereof.

7. The method of paragraph 1, further comprising separating the decomposition mixture into a solid phase and a liquid phase.

8. The method of paragraph 7, wherein the solid phase comprises at least one selected from the group consisting of oligomer, polymer, and combinations thereof.

9. The method of paragraph 8, wherein the solid phase further comprises at least one solid state catalyst.

10. The method of paragraph 7, wherein the liquid phase comprises at least one compound containing at least one carboxyl group.

11. The method of paragraph 10, wherein the at least one compound containing at least one carboxyl group is at least one organic acid.

12. The method of paragraph 11, further comprising converting the at least one organic acid into at least one corresponding ester.

13. The method of paragraph 11, wherein the at least one organic acid is selected from the group consisting of monocarboxylic acid, dicarboxylic acid, polycarboxylic acid, and combinations thereof.

14. The method of paragraph 11, wherein the at least one organic acid is an α,ω-dicarboxylic acid.

15. The method of paragraph 11, wherein the at least one organic acid is selected from the group consisting of 2-methylsuccinic acid, 3-methylglutaric acid, 2,4-dimethylglutaric acid, 2,4-dimethyladipic acid, 3,5-dimethylpimelic acid, 2,4,6-trimethylpimelic acid, 2,4,6-trimethylsebacic acid, 2,4,6,8-tetramethyl-azelaic acid, and combinations thereof.

16. The method of paragraph 11, further comprising separating the at least one organic acid.

17. The method of paragraph 12, further comprising separating the at least one corresponding ester.

18. The method of paragraph 2, wherein the at least one solid state catalyst is selected from the group consisting of zeolite, alumina, silico-alumino-phosphate, sulfated zirconia, zinc oxide, titanium oxide, zirconium oxide, niobium oxide, iron carbonate, calcium carbide, and combinations thereof.

19. The method of paragraph 1, wherein the at least one oxidizing agent is selected from the group consisting of oxygen ($O_2$), nitric oxide (NO), nitrous oxide ($N_2O$), nitrogen dioxide ($NO_2$), nitric acid ($HNO_3$), aqueous nitric acid ($HNO_3$), and combinations thereof.

20. The method of paragraph 3, wherein the temperature range is from 60° C. to 200° C.

21. The method of paragraph 3, wherein the gas is at least one selected from the group consisting of air, nitrogen ($N_2$), oxygen ($O_2$), and combinations thereof.

22. The method of paragraph 3, wherein the initial pressure of the gas is 0 psi to 1000 psi.

23. The method of paragraph 3, wherein the residence time in the reaction vessel is one selected from the group consisting of 30 minutes to 30 hours, less than 30 minutes, and more than 30 hours.

24. The method of paragraph 10, further comprising feeding the oligomer, the polymer, and combinations thereof back into the reactor.

25. The method of paragraph 9, wherein the liquid phase further comprises the at least one oxidizing agent.

26. The method of paragraph 25, further comprising collecting and regenerating the at least one oxidizing agent.

27. The method of paragraph 11, wherein the at least one solid state catalyst is selected from the group consisting of zeolite, alumina, silico-alumino-phosphate, sulfated zirconia, zinc oxide, titanium oxide, zirconium oxide, niobium oxide, iron carbonate, calcium carbide, and combinations thereof.

38. The method of paragraph 14, wherein the at least one corresponding ester is selected from the group consisting of 2-methylsuccinic acid dimethyl ester, 3-methylglutaric acid dimethyl ester, 2,4-dimethylglutaric acid dimethyl ester, 2,4-dimethyladipic acid dimethyl ester, 3,5-dimethylpimelic acid, dimethyl ester, 2,4,6-trimethylpimelic acid dimethyl ester, 2,4,6-trimethylsebacic acid dimethyl ester, 2,4,6,8-tetramethyl-azelaic acid dimethyl ester, and combinations thereof.

This disclosure defines the complete PP chemical recycling system that currently does not exist commercially. The chemical recycling process disclosed herein is unique and addresses a huge plastic waste problem by diverting PP from landfills. This process transforms PP to Product that can be used for value-adding industrial applications (e.g., performance materials, polymers, fibers, compostable plastics, paints and coatings, lubricants, adhesives, fragrances, skincare products, etc.) serving as a drop-in replacement of existing chemical intermediates, or as new chemical intermediates.

In this disclosure, PP is a polymer with many repeating carbon units that is continually broken down into shorter segments and functionalized (e.g., carbon chains can become oxidized forming dicarboxylic acids or monocarboxylic acids). The scission event continues as long-chain polymers depolymerize into gradually shorter-chain species by the Oxidizing Agent until the chain-length has reached a terminal length range and is no longer broken down (e.g., $C_2$-$C_9$ dicarboxylic acids). Alternatively, the reaction process can be controlled to stop the scission event prematurely to achieve chain lengths that are longer than the terminal length range. These various chain lengths are collectively considered Product. To enable the reaction of PP into Product, an appropriate amount of Oxidizing Agent is added to breakdown the polymer into desired chain lengths and the Oxidizing Agent should be at an appropriate concentration as well as PP-to-Oxidizing Agent ratio to produce Product quantities large enough for commercial application. The processes and equipment described in this disclosure allow for control over the process to enable conversion of PP into Product, including terminal reaction species and/or other species of desired chain-lengths.

Both the overall process and individual units are optimized to economically convert PP to Product and minimize use of Oxidizing Agent and Catalyst. The equipment for chemical recycling of PP is designed to optimize process performance metrics within that unit (e.g., the reactor is designed to maximize conversion of PP, the separation units are designed to recover Oxidizing Agent and recycle back to the reactor, and the absorption unit to recover Reaction Gas and regenerate the Oxidizing Agent). These units are designed to minimize energy use and are combined into a process system that recovers and re-uses Oxidizing Agent and Catalyst to minimize the amount made-up in the process. This process is also designed to minimize waste in the gas and liquid phases. Overall, this process can significantly improve the economics of producing Product while diverting PP from waste streams (e.g., landfill and the ocean), extending the lifetime of the carbon. In addition, use of PP for Product reduces the use of petrochemical feedstock that is conventionally used to make Product.

Method to Convert PP into a Reaction Product

Disclosed herein is a method/process to convert PP into a reaction product, or "product," using an Oxidizing Agent and specific operating conditions (e.g., temperatures between 60° C. and 200° C.). This is a chemical reaction that is controlled in a reactor. The problem is that the Oxidizing Agent is partially converted into a Reaction Gas that exits the reactor in the gas phase. To make the process economical, this Reaction Gas is converted back into the Oxidizing Agent and recycled to the reactor. The Product and Oxidizing Agent that remain in the liquid phase are removed from the reactor and the Product is separated. This disclosure details solutions to separate, recover, and recycle the Oxidizing Agent as well as recover the Product.

It should be understood that this invention is not limited to the particular methodologies, protocols, and reagents, etc., described herein and as such can vary therefrom. The terminology used herein is for the purpose of describing particular embodiments only, and is not intended to limit the scope of the present invention, which is defined solely by the claims.

EXAMPLES

The invention is further illustrated by the following examples which are intended to be purely exemplary of the invention, and which should not be construed as limiting the invention in any way. The following examples are illustrative only, and are not intended to limit, in any manner, any of the aspects described herein. The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

The feedstock for this example was PP. This feedstock was food storage containers but different molds including lunch boxes, margarine containers, yogurt pots, syrup bottles, prescription bottles and some plastic bottle caps, all made of PP. These were contaminated with dirt or some level of organic matter and shredded into 0.5 inch to 1.5-inch squares or strips.

Typically, 5 grams (1 to 7 grams) of the PP strips were added to a glass round bottom flask. 100 grams of concentrated nitric acid (20% to 70% nitric diluted with 30 to 80% water) was added to the round bottom flask. The contents in the round bottom flask was heated using a heating mantle to desired temperature of 120° C. (refluxed) while the contents were continuously stirred. Once refluxing started/ desired temperature was reached, the reaction continued for 6 hours (1 to 24 hours). After the completion of reaction, the round bottom flask was cooled down to room temperature. The reaction generates significant amount of gases that escape during the reaction. The reaction conditions are summarized in Table 1.

The final mixture consisted of solids (unreacted/partially reacted PP), liquid solution (nitric acid and water mixture) and products dissolved in the liquid solution. The liquid solution was pipetted out to separate it from the solids or the solids were separated using a glass fiber filter paper. The liquid solution was then decanted into a glass beaker and nitric acid/water mixture was evaporated overnight at 60° C. The left-over products in the glass beaker were analyzed on various analytical instruments for its chemical composition.

ously stirred. Once the internal temperature of the reaction vessel reached the target temperature, the reaction continued for 120 min (2 hours). After 2 hours (completion of reaction), the reactor was cooled down to room temperature with continuous stirring. The reaction generated significant amount of gases which leaves the reactor under pressure (10-100 psi) even after cool down. The reaction conditions are summarized in Table 1.

Once the reactor cooled down, the gases were vented and the reactor was purged with inert gas to remove trapped gases. The final mixture consisted of solids (unreacted/partially reacted PP), liquid solution (nitric acid and water mixture) and products dissolved in the liquid solution. The liquid solution was pipetted out to separate it from the solids or the solids were separated using a glass fiber filter paper. The liquid solution was then decanted into a glass beaker and nitric acid/water mixture was evaporated overnight at 60° C. The left-over products in the glass beaker were analyzed on various analytical instruments for its chemical composition.

TABLE 1

| expt number | open/closed vessel | $HNO_3$ conc (wt %) | solution:solids ratio (w/w) | target temp (° C.) | max temp observed | max pressure observed (psig*) | time at temp (h) | mass lost as gases during reaction (%) | solids recovered (%) |
|---|---|---|---|---|---|---|---|---|---|
| 1.1 | open | 25 | 20:1 | reflux | reflux | 0 | 6 | Not recorded | 100 |
| 1.2 | open | 50 | 20:1 | reflux | reflux | 0 | 6 | Not recorded | 109 |
| 1.3 | open | 70 | 20:1 | reflux | reflux | 0 | 6 | −14.1 | Not recorded |
| 1.4 | open | 50 | 10:1 | reflux | reflux | 0 | 6 | −2.3 | 115 |
| 1.5 | open | 70 | 10:1 | reflux | reflux | 0 | 6 | −17.8 | 88 |
| 1.6 | open | 50 | 20:1 | reflux | reflux | 0 | 24 | −6.4 | 59 |
| 1.7 | open | 70 | 20:1 | reflux | reflux | 0 | 24 | −14.7 | 37 |
| 1.8 | open | 50 | 20:1 | reflux | reflux | 0 | 1 | −0.7 | 102 |
| 1.9 | open | 70 | 20:1 | reflux | reflux | 0 | 1 | −3.3 | 107 |
| 1.10 | open | 50 | 70:1 | reflux | reflux | 0 | 6 | −0.3 | 117 |
| 1.11 | open | 70 | 70:1 | reflux | reflux | 0 | 6 | −5.6 | 53 |
| 2.1 | closed | 70 | 20:1 | 120 | 139 | 248 | 2 | Not recorded | Not recorded |
| 2.2 | closed | 25 | 7:1 | 160 | 169 | 851 | 2 | Not recorded | 94% |
| 2.3 | closed | 25 | 7:1 | 180 | 194 | 1635 | 2 | Not recorded | 78% |
| 2.4 | closed | 25 | 7:1 | 200 | 225 | 2539 | 2 | Not recorded | 84% |

*psig is gauge pressure.

Example 2

The feedstock for this example was PP. This feedstock were food storage containers of different molds including lunch boxes, margarine containers, yogurt pots, syrup bottles, prescription bottles and some plastic bottle caps made of PP. These were contaminated with dirt or some level of organic matter and shredded into 0.5-inch to 1.5-inch squares or strips.

Typically, 5 grams (1 to 7 grams) of the PP strips were placed in a glass liner. 100 grams of concentrated nitric acid (20% to 70% nitric diluted with 30 to 80% water) was added to the liner and loaded into the reactor vessel. The reactor was sealed, purged with inert gas (nitrogen/argon/helium) and the reactor was pressurized with air between 0 psi to 600 psi. Then, the reactor was heated to desired temperature of 120° C. (120 to 150° C.) while the contents were continu- Table 2 shows the products of the reaction as determined by LCMS.

TABLE 1

Summary of typical LCMS results from Example 2.

| Retention time | m/z (—) | Assignment | Comment |
|---|---|---|---|
| 1.514 | 147 | | |
| 1.813 | 143 | | |
| 1.902 | 131 | 2-methylsuccinic acid | Matches commercial sample |
| 2.104 | 145 | 3-methylglutaric acid | Matches commercial sample |
| 2.201 | 157 | | |
| 2.260 | 189 | | |
| 2.387 | 229 | | |

TABLE 1-continued

Summary of typical LCMS results from Example 2.

| Retention time | m/z (—) | Assignment | Comment |
|---|---|---|---|
| 2.484 | 157 | | |
| 2.618 | 159 | 2,4-dimethylglutaric acid | Matches commercial sample |
| 2.991 | 173 | 2,4-dimethyladipic acid | |
| 3.268 | 187 | 3,5-dimethylpimelic acid | |
| 3.417 | 271, 285 | | |
| 3.775 | 201 | 2,4,6-trimethylpimelic acid | |
| 4.051 | 215 | 2,4,6-trimethylsebacic acid | |
| 4.454 | 313 | | |
| 4.700 | 243 | 2,4,6,8-tetramethyl-azelaic acid | |
| 4.916 | 495 | | |
| 5.677 | 579 | | |

Table 3 depicts a summary of typical GCMS results from Example 2 (with peaks representing >1% of total peak area).

TABLE 3

| Pk# | RT | Area % | Library/ID | Ref# | CAS# | Qual |
|---|---|---|---|---|---|---|
| 3 | 9.181 | 8.17 | C:\Database\NIST11.L | | | |
| | | | Butanedioic acid, methyl-, dimethyl ester | 31111 | 001604-11-1 | 91 |
| | | | Butanedioic acid, methyl-, dimethyl ester | 31113 | 001604-11-1 | 83 |
| | | | Butanedioic acid, methyl-, dimethyl ester | 31114 | 001604-11-1 | 74 |
| 5 | 10.879 | 4.57 | C:\Database\NIST11.L | | | |
| | | | Pentanedioic acid, 2,4-dimethyl-, dimethyl ester | 52114 | 002121-68-8 | 38 |
| | | | 1,4-Benzenedicarbonitrile, 2-formyl- | 29171 | 164932-42-7 | 12 |
| | | | 1H-Cyclopenta[c]thiophene, hexahydro-, cis- | 12355 | 053907-80-5 | 10 |
| 6 | 11.234 | 15.21 | C:\Database\NIST11.L | | | |
| | | | Pentanedioic acid, 2,4-dimethyl-, dimethyl ester | 52114 | 002121-68-8 | 86 |
| | | | 1H-Cyclopenta[c]thiophene, hexahydro-, cis- | 12355 | 053907-80-5 | 14 |
| | | | Furan, 2-methyl-5-(methylthio)- | 12169 | 013678-59-6 | 12 |
| 10 | 12.443 | 13.22 | C:\Database\NIST11.L | | | |
| | | | 5-Acetoxy-3-methyl-hexanoic acid, methyl ester | 62293 | 1000192-54-4 | 94 |
| | | | 9-Decenoic acid, 2,4-dimethyl-, methyl ester, (R,R)-(−)- | 71142 | 031183-23-0 | 38 |
| | | | Heptanedioic acid, 2-methyl-, dimethyl ester | 62286 | 033658-48-9 | 38 |
| 12 | 13.719 | 2.60 | C:\Database\NIST11.L | | | |
| | | | Heptanedioic acid, 3,5-dimethyl-, dimethyl ester | 73901 | 104116-37-2 | 90 |
| | | | Quinoline, 2-butyl- | 49554 | 007661-39-4 | 43 |
| | | | Cyclohexanecarboxylic acid, ethyl ester | 29080 | 003289-28-9 | 25 |
| 13 | 13.974 | 16.53 | C:\Database\NIST11.L | | | |
| | | | 3-Cyclobut-1-enyl-3-hydroxy-2-methyl-propionic acid, methyl ester | 38916 | 1000190-69-7 | 27 |
| | | | Adipic acid, methyl propyl ester | 62256 | 1000324-51-9 | 27 |
| | | | Methyl 2-methyl-3-cyclopropylpropanoate | 19804 | 062021-35-6 | 22 |
| 16 | 15.129 | 10.03 | C:\Database\NIST11.L | | | |
| | | | 2-Propanone, 1-cyclopentyl-3-ethoxy- | 38039 | 051149-71-4 | 14 |
| | | | Cyclohexane, 1,2-diethyl-, cis- | 18036 | 000824-43-1 | 11 |
| | | | Cyclohexane, 1,2-diethyl-3-methyl- | 27092 | 061141-80-8 | 11 |
| 17 | 16.338 | 6.86 | C:\Database\NIST11.L | | | |
| | | | Octanedioic acid, 2,2,7,7-tetramethyl- | 85774 | 016386-99-5 | 43 |
| | | | 9-Decenoic acid, 2,4-dimethyl-, methyl ester, (2S,4R)-(+)- | 71145 | 031183-24-1 | 14 |
| | | | O-Fluoroacetophenone oxime | 26538 | 000364-81-8 | 11 |
| 20 | 17.426 | 2.01 | C:\Database\NIST11.L | | | |
| | | | meta-Methoxybenzenethiol | 18376 | 015570-12-4 | 15 |
| | | | Cyclohexanone, 2-(1-mercapto-1-methylethyl)-5-methyl-, trans- | 49945 | 033281-91-3 | 15 |
| | | | Benzenethiol, 4-methoxy- | 18378 | 000696-63-9 | 15 |
| 23 | 19.079 | 1.16 | C:\Database\NIST11.L | | | |
| | | | Dibenzo[b,f]oxepin-3-ylamine | 68691 | 1000304-76-7 | 35 |
| | | | Carbamic acid, (4-ethoxyphenyl)-, ethyl ester | 68521 | 1000319-47-6 | 35 |
| | | | Quinoline, 2-(1-methyl-1H-imidazol-4-yl)- | 68651 | 002552-96-7 | 30 |

TABLE 3-continued

| Pk# | RT | Area % | Library/ID | Ref# | CAS# | Qual |
|---|---|---|---|---|---|---|
| 24 | 19.268 | 1.75 | C:\Database\NIST11.L | | | |
| | | | 2,8-Bis(1,5,5-trimethylpyrrolidin-2,4-dion-3-ylidene)-3,7-diazanonan | 213610 | 1000286-75-3 | 50 |
| | | | 2-Amino-3,5,7,8-tetrahydro-4,6-pteridinedione | 46535 | 001011-23-0 | 38 |
| | | | 1,2-Dimethoxy-4-(1,2-dimethoxyethyl)benzene | 82440 | 1000333-50-1 | 27 |

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Various embodiments of this application are described herein, including the best mode known to the inventors for carrying out the application. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed is:

1. A method for decomposing polypropylene (PP) waste, comprising:
   a. adding PP waste to a reaction vessel;
   b. adding at least one oxidizing agent to the reaction vessel to give a mixture, wherein the at least one oxidizing agent is aqueous nitric acid ($HNO_3$); and c. subjecting the mixture obtained in b. to conditions effective to decompose the PP waste to produce decomposition products, wherein the decomposition products comprise at least one dicarboxylic acid optionally substituted by a nitro group; or the salts or esters or anhydrides thereof.

2. The method of claim 1, wherein the decomposition products further comprise at least one carboxylic acid, optionally substituted by a nitro group.

3. The method of claim 1, wherein the PP waste further comprises at least one plastic material; and at least one non-plastic material.

4. The method of claim 3, wherein the plastic material is selected from the group consisting of plastic film, plastic foam, plastic packaging, plastic bags, plastic wrap, and combinations thereof.

5. The method of claim 3, wherein the non-plastic material is selected from the group consisting of non-plastic organic material, inorganic material, fluid, and combinations thereof.

6. The method of claim 1, wherein the nitric acid has a concentration of 10-100 wt %.

7. The method of claim 1, wherein the nitric acid has a concentration of about 67 to about 70 wt %.

8. The method of claim 1, wherein the weight ratio of nitric acid to PP is at least 3:1.

9. The method of claim 1, wherein the weight ratio of nitric acid to PP is at least 10:1.

10. The method of claim 1, wherein the conditions comprise a temperature range from 60° C. to 200° C.

11. The method of claim 1, wherein the conditions comprise an initial pressure range of 0 psi to 1000 psi.

12. The method of claim 7, wherein the conditions comprise the presence of a gas that is at least one selected from the group consisting of air, nitrogen ($N_2$), oxygen ($O_2$), and combinations thereof.

13. The method of claim 1, wherein the conditions comprise a residence time in the reaction vessel of 30 minutes to 30 hours.

14. The method of claim 1, wherein the dicarboyxlic acid or dicarboxylic acid substituted with at least one nitro group is substituted with one or more methyl groups.

15. The method of claim 1, wherein the decomposition products comprise at least one $C_4$-$C_{15}$ dicarboxylic acid.

16. The method of claim 1, further comprising adding at least one solid state catalyst to the reaction vessel.

17. The method of claim 16, wherein the at least one solid state catalyst is zeolite, alumina, silico-alumino-phosphate, sulfated zirconia, zinc oxide, titanium oxide, zirconium oxide, niobium oxide, iron carbonate, calcium carbide, or combinations thereof.

18. The method of claim 1, further comprising separating the decomposition products into a solid phase and a liquid phase.

19. The method of claim 18, wherein the solid phase comprises at least one of oligomer, polymer, or combinations thereof.

20. The method of claim 18, wherein the solid phase further comprises at least one solid state catalyst.

21. The method of claim 18, wherein the liquid phase comprises a carboxylic acid, dicarboxylic acid, carboxylic acid substituted with a nitro group, or dicarboxylic acid substituted with a nitro group, or the salt, or ester or anhydride thereof.

22. The method of claim 2, further comprising converting the carboxylic acid optionally substituted with a nitro group and/or the dicarboxylic acid optionally substituted with a nitro group into an ester.

23. The method of claim 2 further comprising separating the carboxylic acid optionally substituted with a nitro group and/or the dicarboxylic acid optionally substituted with a nitro group, or the salts, or esters or anhydrides thereof.

24. The method of claim 22, further comprising separating the at least one corresponding ester.

25. The method of claim 24, wherein the ester is at least one of 2-methylsuccinic acid, dimethyl ester; 3-methylglutaric acid, dimethyl ester; 2,4-dimethylglutaric acid, dimethyl ester; 2,4-dimethyladipic acid, dimethyl ester; 3,5-diethylpimelic acid, dimethyl ester; 2,4,6-trimethylpimelic acid, dimethyl ester; 4,6-trimethylsebacic acid, dimethyl ester; 2,4,6,8- tetramethyl-azelaic acid; or a combination thereof.

26. The method of claim 19, further comprising feeding the oligomer, the polymer, and combinations thereof back into the reaction vessel.

27. The method of claim 18, wherein the liquid phase further comprises the at least one oxidizing agent.

28. The method of claim 27, further comprising collecting and regenerating the at least one oxidizing agent.

29. A composition, comprising a mixture of 2-methylsuccinic acid, or a salt, ester, or anhydride thereof; 3-methylglutaric acid, or a salt, ester, or anhydride thereof; 2,4-dimethylglutaric acid, or a salt, ester, or anhydride thereof; 2,4-dimethyladipic acid, or a salt, ester, or anhydride thereof; 3,5-dimethylpimelic acid, or a salt, ester, or anhydride thereof; 2,4,6-trimethylpimelic acid, or a salt, ester, or anhydride thereof; 2,4,6-trimethylsebacic acid, or a salt, ester, or anhydride thereof; and 2,4,6,8-tetramethyl-azelaic acid, or a salt, ester, or anhydride thereof.

30. The composition of claim 29, further comprising at least one of dimethyl 2-methylbutanedioate; dimethyl 2,4-dimethylpentanedioate; 2-formylbenzene-1,4-dicarbonitrile; methyl 5-acetyloxy-3-methylhexanoate; methyl 2,4- dimethyldec-9-enoate; dimethyl 2-methylheptanedioate; dimethyl 3,5-dimethylheptanedioate; 2-butylquinoline; ethyl cyclohexanecarboxylate; 3-cyclobut-1-enyl-hydroxy-2-methyl-propionic acid, methyl ester; 1-O-methyl 6-O-propyl hexanedioate; methyl 2-methyl-3-cyclopropylpropanoate; 1-cyclopentyl-3-ethoxypropan-2-one; (1R,2S)-1,2- diethylcyclohexane; 1,2-diethyl-3-methylcyclohexane; 2,2,7,7-tetramethyloctanedioic acid; methyl (2S,4R)-2,4-dimethyldec-9-enoate; O-fluoroacetophenone oxime; (2R, 5R)-2-(2-mercaptopropan-2-yl)-5-methylcyclohexan-1-one; dibenzooxepin-3-ylamine; ethyl (4-ethoxyphenyl)carbamate; 2-(1-methyl-1H-imidazol-4yl)quinoline; 2,8-bis(1,5,5-trimethylpyrrolidin-2,4-dion-3-ylidene)-3,7-diazanonan; 2-amino-3,5,7,8-tetrahydro-4,6-pteridinedione; or 1,2-dimethoxy-4-(1,2-dimethoxyethyl)benzene, or a salt, ester or anhydride thereof.

* * * * *